United States Patent
Faris

Patent Number: 5,451,785
Date of Patent: Sep. 19, 1995

[54] UPCONVERTING AND TIME-GATED TWO-DIMENSIONAL INFRARED TRANSILLUMINATION IMAGING

[75] Inventor: Gregory W. Faris, Menlo Park, Calif.

[73] Assignee: SRI International, Menlo Park, Calif.

[21] Appl. No.: 215,123

[22] Filed: Mar. 18, 1994

[51] Int. Cl.⁶ .................. G01N 21/25; G01N 21/47; A61B 6/00
[52] U.S. Cl. .................. 250/330; 128/664; 250/358.1
[58] Field of Search .............. 250/330, 332, 358.1; 128/664

[56] References Cited

U.S. PATENT DOCUMENTS 5,216,667  5/1993  Tomlinson, Jr. et al. ............ 367/7

OTHER PUBLICATIONS

Firester, "Image Upconversion: Part III," Journal of Applied Physics, vol. 41, No. 2 (Feb. 1970), pp. 703–709.
Andersson-Engels et al., "Time-resolved Transillumination for Medical Diagnostics," Optics Letters, vol. 15, No. 21 (Nov. 1990), pp. 1179–1181.
Hebden et al., "Time Resolved Imaging through a Highly Scattering Medium," Applied Optics, vol. 30, No. 7 (Mar. 1991) pp. 788–794.
Yoo et al., "Imaging Objects Hidden in Highly Scattering Media Using Femtosecond Second-Harmonic-Generation Cross-correlation Time Gating," Optics Letters, vol. 16, No. 13 (Jul. 1991) pp. 1019–1021.
Yoo et al., "Imaging through a Scattering Wall Using Absorption," Optics Letters, vol. 16, No. 14 (Jul. 1991) pp. 1068–1070.
Duncan et al., "Time-Gated Imaging through Scattering Media Using Stimulated Raman Amplification," Optics Letters, vol. 16, No. 23 (Dec. 1991) pp. 1868–1870.
Benaron, "Measuring and Imaging in Tissue Using Near-IR Light," Optics & Photonics News, (Oct. 1992) pp. 27–31.
Svanberg, "Optical Tissue Diagnostics: Fluorescence and Transillumination Imaging," Optics and & Photonics News, (Oct. 1992) pp. 31–34.
Yan et al., "Imaging with Femtosecond Pulses," Applied Optics, vol. 31, No. 32 (Nov. 1992) pp. 6869–6873.

(List continued a next page.).

*Primary Examiner*—Carolyn E. Fields
*Assistant Examiner*—Edward J. Glick
*Attorney, Agent, or Firm*—Elliot B. Aronson

[57] ABSTRACT

A method and apparatus for direct two-dimensional transillumination imaging of a sample immersed in or including a scattering medium at infrared to near-infrared wavelengths. Frequency conversion and time-gating techniques in the infrared and near-infrared range are used to enhance two-dimensional image collection and detection. The apparatus includes a probe radiation source for applying a probe beam in the infrared to near-infrared frequency range to the sample. The probe beam is spread to cover a two-dimensionally extending area of the sample to be imaged. After interacting with the sample, the probe beam is representative of a two-dimensional image of the covered sample area. In one embodiment the apparatus includes a time-gating arrangement for selecting a temporal portion of the probe beam in a narrow time window representative of early arriving photons transmitted through the scattering medium and providing a time-gated beam representative of the two-dimensional image of the sample area. A reference beam interacts with a nonlinear medium to shift the frequency of the probe beam to a different frequency, which may lie outside the infrared to near-infrared range. In many applications of the apparatus the frequency will be shifted upward to a frequency higher than near-infrared. The nonlinear interaction occurs in such a manner so as not to destroy the two-dimensional image carrier by the time-gated beam. A detector operative at the shifted frequency detects the time-gated and frequency-shifted beam to directly record the two-dimensional image.

5 Claims, 3 Drawing Sheets

OTHER PUBLICATIONS

Benaron et al., "Optical Time-of-Flight and Absorbance Imaging of Biologic Media," Science, vol. 259 (Mar. 1993) pp. 1463–1466.

Das et al., "Ultrafast Time-Gated Imaging in Thick Tissues: A Step Toward Optical Mammography," Optics Letters, vol. 18, No. 13 (Jul. 1993) pp. 1092–1094.

Hee et al., "Femtosecond Transillumination Tomography in Thick Tissues," Optics Letters, vol. 18, No. 13 (Jul. 1993) pp. 1107–1109.

Bashkansky et al., "Nonlinear-Optical Field Cross-Correlation Techniques for Medical Imaging with Lasers," Applied Optics, vol. 32, No. 21 (Jul 1993) pp. 3842–3845.

Kalpaxis et al., "Three-Dimensional Temporal Image Reconstruction of an Object Hidden in Highly Scattering Media by Time-Gated Optical Tomography," Optics Letters, vol. 18, No. 20 (Oct. 1993) pp. 1691–1693.

Firester, "Upconversion: A New Technique for Infrared to Visible Conversion", IEEE International Convention Digest, 1970, pp. 22–23.

Keyukov et al., "Transverse Up-Conversion Method for Recording Infrared Radiation with Picosecond Time Resolution", Soviet Journal of Quantum Electronics, vol. 5, No. 10, 1975, pp. 1236–1239.

Stappaerts et al., "Efficient IR Up-conversion in Two-Photon Resonantly Pumped Cs Vapor", Appl. Phys. Lett, vol. 29, No. 10, 1976, pp. 669–670.

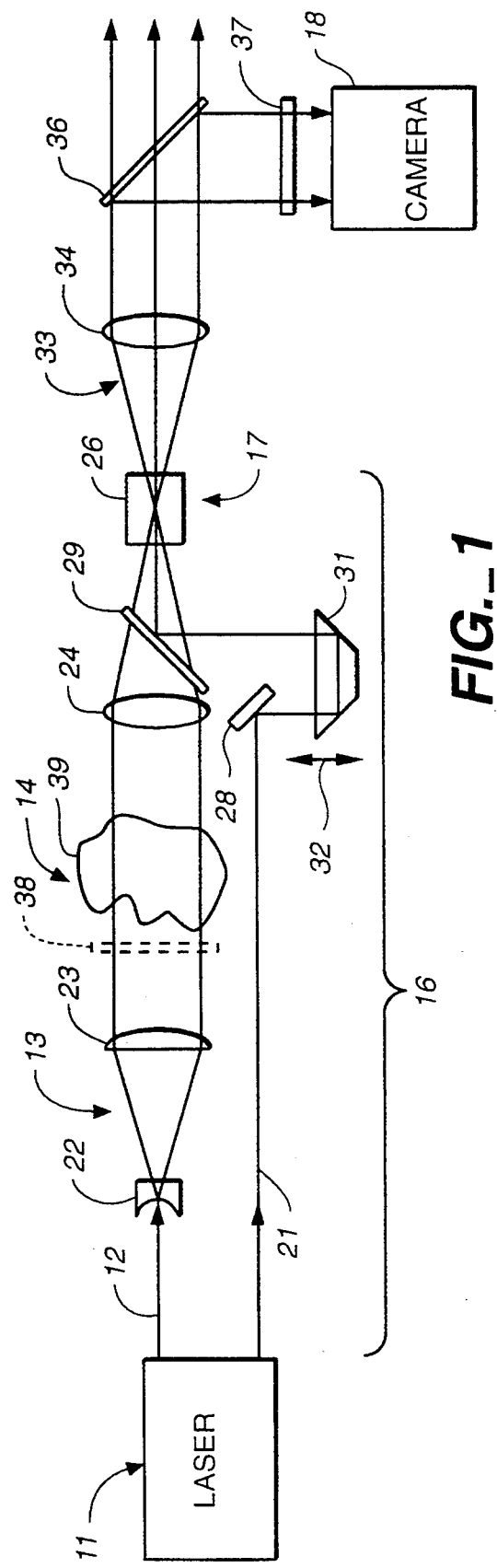
FIG._1

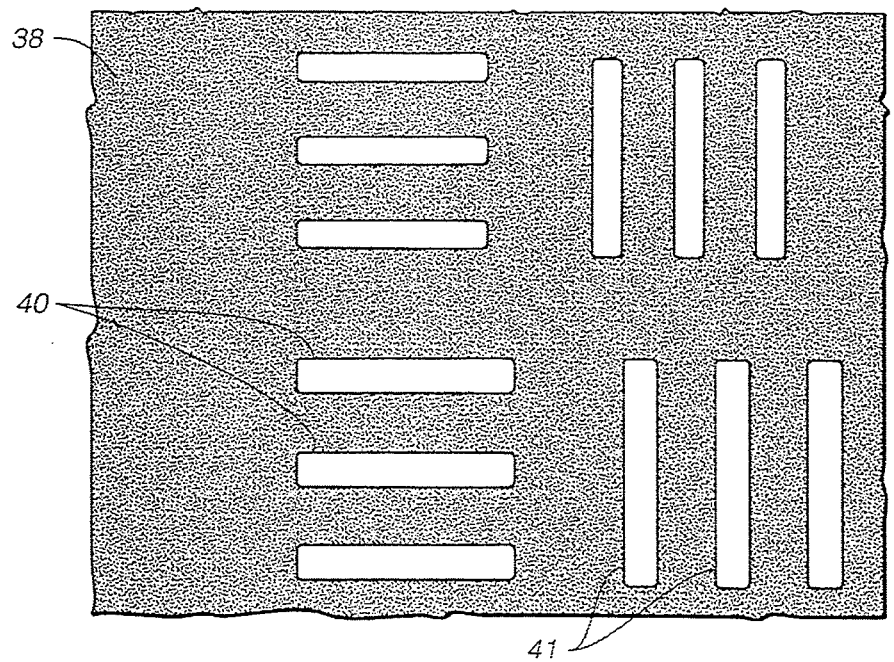
FIG._2
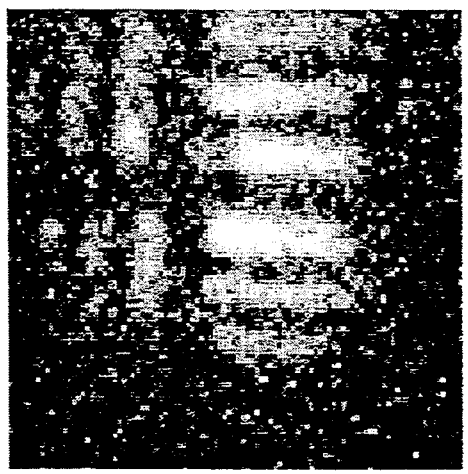
FIG._3
←→
1 mm
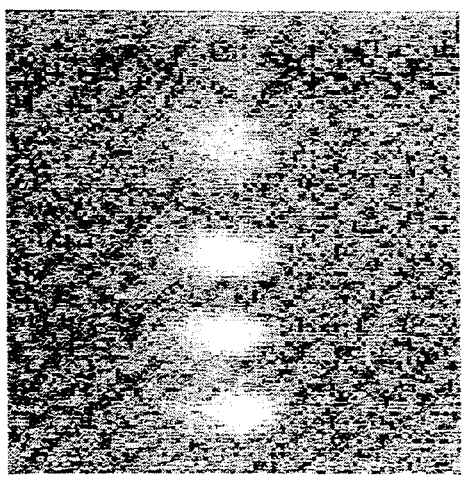
FIG._5
←→
1 mm

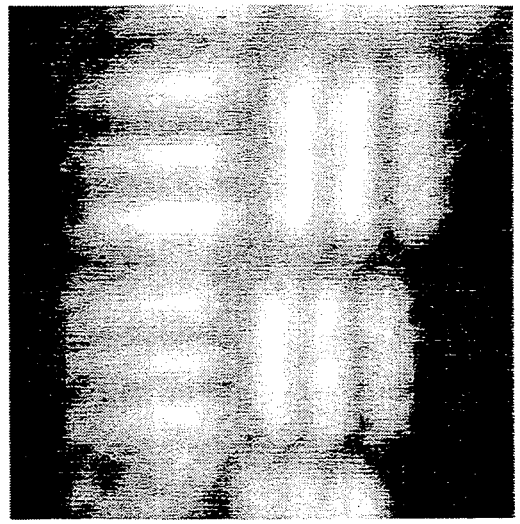
*FIG._4A*
1 mm
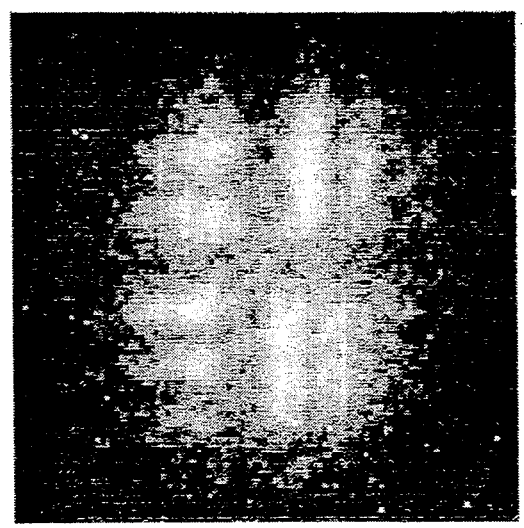
*FIG._4B*
1 mm
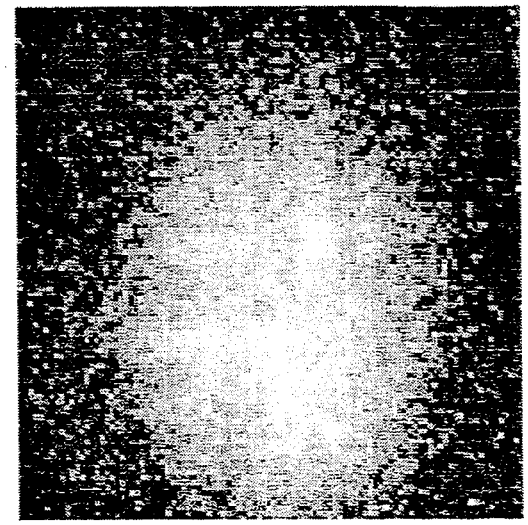
*FIG._4C*
1 mm

UPCONVERTING AND TIME-GATED TWO-DIMENSIONAL INFRARED TRANSILLUMINATION IMAGING

BACKGROUND OF THE INVENTION

The present invention relates to transillumination imaging techniques used in medical or other applications for obtaining images of interior details in a living body or of other objects, and is more particularly directed to imaging techniques using infrared or near-infrared radiation.

Optical transillumination imaging is an imaging technique that shows promise as an alternative to x-rays, magnetic resonance, ultrasound, positron emission, thermal emission, or other techniques for forming images of certain internal details of a living body. The body portion or object to be imaged is illuminated with a source of radiation in the visible, infrared, or near-infrared range, and the body portion or object selectively absorbs, scatters and transmits the radiation to form an image that is recorded by a suitable detecting apparatus. Differences in absorption or scattering characteristics of the object under examination may lead to discernable features in the recorded image. For example, transillumination of tissue may provide a useful diagnostic modality for malignant tumors, which often exhibit greater attenuation or different scattering of light compared with neighboring healthy tissue, possibly due to a plentiful supply of blood and high concentration of mitochondria in the tumor.

Optical transillumination is potentially highly attractive in that it is noninvasive and nondestructive (the radiation is non-ionizing), optical radiation can be tolerated in comparatively large doses by the patient, it poses no radiation danger to the attending personnel, and it can reveal features not readily discernable by other techniques. In comparison with x-rays, for example, infrared or near-infrared radiation is more sensitive to soft tissue variations and gives appreciably better contrast. X-rays, however, provide extremely good spatial resolution (down to 100 microns), but at the sacrifice of good contrast.

Although infrared and near-infrared transillumination provides good contrast, it gives poor resolution, resulting in blurred images, in great part because of scattering. At infrared and near-infrared wavelengths, the radiation is strongly scattered as it passes through the tissue and surrounding medium. Radiation in this spectral range typically undergoes multiple scattering events before it emerges from the sample. The scattering events effectively smear out the spatial resolution.

Past efforts to improve infrared imaging have included improvements in infrared sources for transillumination through the body (e.g., cooler light sources using fiber optic bundles so as to avoid the possibility of burning the patient) and improvements in infrared cameras for better detection. Scattering of the infrared radiation as it passes through body tissue, however, remains a key problem in obtaining clear images.

A number of attempts have been made to reduce or eliminate the effects of scattered light. See, for example, D. A. Benaron, "Measuring and Imaging in Tissue Using Near-IR Light," *Optics & Photonics News*, (October 1992), p. 27, and S. Svanberg, "Optical Tissue Diagnostics: Fluorescence and Transillumination Imaging," *Optics & Photonics News*, (October 1992), p. 31, and references cited therein. One approach to the problem makes use of so-called time-resolved methods. Time-resolved methods discriminate photons of light received at the detector based on the time taken to transit the sample. In one form of time-resolved method all the photons traversing the sample are detected and their arrival times are recorded. The image is then mathematically reconstructed from the photon delays as they travel from the emitter to the detector. In another method an attempt is made to receive only the so-called ballistic photons, which are those that traverse the sample with no scattering. In the absence of scattering, the photon path is linear and conventional radiological analysis may be used to view and interpret the image. This method, sometimes referred to as time-gating, has the advantage that it avoids the computationally complex image reconstruction called for in the more general time-resolved method where all photons are detected and used to construct the image. Time-gating is based on the concept that light which exits a transilluminated sample earlier has traveled a shorter and straighter path in the sample than light exiting later. The earlier light has undergone fewer scattering events and thus contains more information about the spatial localization of absorption within the sample. Time-gating methods then seek to detect only the early-arriving light and to block out the later-arriving light. The problem with these methods is that in a strong scattering environment there are not many ballistic photons to be detected. This places demanding requirements on the detector and often calls for averaging techniques to improve the signal-to-noise characteristics which can wash out information about the image.

Time-gating has been applied in various contexts. For time-gating studies applied specifically to imaging of tissue, see for example the work of S. Andersson-Engels et al., "Time-resolved transillumination for medical diagnostics," *Optics Letters*, Vol. 15 (November 1990), p. 1179, or M. R. Hee et al., "Femtosecond transillumination optical coherence tomography," *Optics Letters*, Vol. 18 (June 1993), p. 950, or L. L. Kalpaxis et al., "Three-dimensional temporal image reconstruction of an object hidden in highly scattering media by time-gated optical tomography," *Optics Letters*, Vol. 18 (October 1993), p. 1691.

Another technique which has been investigated in other contexts for processing images is known as optical upconversion. According to this technique the object under investigation is illuminated with radiation at a first frequency and the image beam carrying the image information is converted to a higher frequency at which it is more amenable to detection and processing. Extensive studies of upconversion are reported by A. H. Firester in a series of articles, see A. H. Firester, "Image Upconversion: Part III," *Journal of Applied Physics*, Vol. 41 (February 1970), p. 703, which cites the earlier articles in the series.

In a recent article M. Bashkansky and J. Reintjes report on a time-gated transillumination system that also has the potential for upconversion or downconversion of the image to more convenient wavelengths. M. Bashkansky and J. Reintjes, "Nonlinearoptical field cross-correlation techniques for medical imaging with lasers," *Applied Optics*, Vol. 32 (July 1993), p. 3842. The Bashkansky and Reintjes system has the shortcoming that it is inherently one-dimensional. To obtain an image, which is necessarily two-dimensional, the object must be scanned with a plurality of one-dimensional elements, and the image is constructed one line at a time.

Many of the time-resolved optical transillumination systems reported in the literature rely on wavelengths in the visible region of the spectrum. For transillumination of living tissue, however, there is a useful window of wavelengths between about 600 nanometers (nm) and about 1300 nm. At the 600 nm end of the range blood absorption falls off strongly and at the 1300 nm end of the range water absorption increases rapidly. It has been observed that within this range, however, tissue absorbance is comparatively low, permitting a greater transmitted light signal to be detected. For the longer wavelengths above about 1000 nm scattering effects are also less pronounced, leading to more ballistic photons. Nevertheless, good tissue transillumination imaging schemes are not available in this spectral range because of the lack of detectors with good sensitivity and low noise in this spectral region and because many of the reported transillumination schemes are not particularly suited to this wavelength range.

SUMMARY OF THE INVENTION

The present invention provides for direct two-dimensional transillumination imaging of a sample immersed in or including a scattering medium at infrared to near-infrared wavelengths. The invention produces an image without the need for constructing the image from one-dimensional scan lines and without the need for other more complex reconstruction schemes. The invention achieves this result through the application of frequency conversion and time-gating techniques in the infrared and near-infrared range to enhance two-dimensional image collection and detection. Briefly, apparatus according to the invention includes a probe radiation source for applying a probe beam in the infrared to near-infrared frequency range to the sample. The probe beam is spread to cover a two-dimensionally extending area of the sample to be imaged. After interaction with the sample the probe beam will be representative of a two-dimensional image of the area. In one embodiment the apparatus includes a time-gating arrangement for selecting a temporal portion of the probe beam in a narrow time window representative of early arriving photons transmitted through the scattering medium and providing a time-gated beam representative of the two-dimensional image of the sample area. A reference beam interacts with a nonlinear medium to shift the frequency of the probe beam to a different frequency, which may lie outside the infrared to near-infrared range. In many applications of the apparatus the frequency will be shifted upward to a frequency higher than near-infrared. The nonlinear interaction occurs in such a manner so as not to destroy the two-dimensional image carried by the time-gated beam. A detector operative at the shifted frequency detects the time-gated and frequency-shifted beam to directly record the two-dimensional image. When imaging in particular environments, the apparatus may sometimes provide useful images when either the time-gating or the frequency conversion is relaxed as described below.

Other aspects, advantages, and novel features of the invention are described below or will be readily apparent to those skilled in the art from the following specifications and drawings of illustrative embodiments.

BRIEF DESCRIPTION OF THE DRAWINGS

FIG. 1 is a schematic block diagram of an embodiment of apparatus for practicing the invention.

FIG. 2 is a plan view of a portion of a resolution test target used to obtain the test results shown in FIGS. 3-5.

FIG. 3 is a plot of image data recorded by a ccd camera using the resolution test target of FIG. 2 and a cw mode-locked laser.

FIGS. 4A, 4B and 4C are plots of image data recorded by a ccd camera in various scattering environments using the resolution test target of FIG. 2 and a Q-switched mode-locked laser.

FIG. 5 is a plot of image data recorded by a ccd camera from a single pulse of a Q-switched mode-locked laser using a difference-frequency upconversion time gate.

DETAILED DESCRIPTION OF ILLUSTRATIVE EMBODIMENTS

An embodiment of transillumination imaging apparatus according to the invention is shown schematically in FIG. 1. A radiation source 11 provides a probe radiation beam 12 of a selected frequency generally falling in the infrared or near infrared range. An optical arrangement indicated generally at 13 directs radiation beam 12 onto a sample under investigation 14 and spreads the beam to cover a two-dimensional area of the sample. The system includes a time-gate subsystem indicated generally at 16 for selecting a temporal portion of beam 12 indicative of photons that are unscattered or little-scattered by the sample. As will be evident from the discussion below, the time-gated beam carries a representation of a two-dimensional image of the two-dimensional area of the sample illuminated by the incident beam 12. An upconversion arrangement indicated generally at 17 shifts the time-gated beam, in a manner so as not to destroy the image information carried in the beam, to an upconverted frequency higher than the frequency of the incident beam that illuminates the sample. A detector 18 operates at the upconversion frequency to detect the time-gated beam representative of the two-dimensional image.

In one embodiment of the apparatus radiation source 11 was provided by a Coherent Antares continuous-wave, mode-locked Nd:YAG laser providing a probe beam 12 of 1064 nm wavelength (infrared) and also providing a reference or pump beam 21 at the second harmonic wavelength of 532 nm (green), which is used in the time-gate subsystem. The cw laser provides a continuous pulse train with pulse lengths of 90 picoseconds (ps). In another configuration of the apparatus the cw laser was replaced with a Continuum PY61C-10 Q-switched mode-locked laser providing probe and reference beams at the same wavelengths as the cw laser. The Q-switched laser pulse lengths were about 35 ps. Optical arrangement 13 includes the lenses 22, 23 and 24. Lens pair 22 and 23 expands the probe beam to cover the two-dimensional area of the sample to be imaged. Lens 24 placed after sample 14 focuses the image-bearing beam onto a KDP (potassium dihydrogen phosphate) crystal 26. In the apparatus of FIG. 1 the KDP crystal serves a dual role. It performs the gating function of time-gate subsystem 16, and it performs the upconversion function. The crystal accomplishes the gating function by enabling the probe and reference beams 12 and 21 to interact with one another and produce the time-gated beam. The KDP crystal also has the appropriate nonlinear characteristics to generate the sum or difference frequencies of the input beams so that the beam emerging from the crystal in the arrangement of FIG. 1 is both time-gated and upconverted. Although a KDP crystal is illustrated here, other crystals may also be used such as BBO (beta barium borate) and LBO (lithium triborate). To reduce the loss of spatial resolution due to the finite length of crystal 26 the distances from sample 14 to lens 24 and from lens 24 to crystal 26 were both equal to one focal length of lens 24. Lens 24 is illustrated diagrammatically in FIG. 1 as a single lens. In a practical system, however, lens 24 will generally correspond to a multiple lens assembly for the following reason. The transverse dimensions of probe beam 12 at the sample are wide enough to cover a substantial two-dimensional area of the sample and are preferably as wide as the total area to be imaged. With a single lens 24 the larger the beam transverse dimension is at the sample, the smaller it will be at crystal 26. For a sufficiently intense beam, a narrow beam dimension at the crystal could result in damage to the crystal. A multiple lens array counteracts this tendency by allowing a bigger spot on the crystal to be formed.

Time-gating subsystem 16 was provided by the 532-nm wavelength reference beam 21 together with mirrors 28 and 29, movable pdsm 31 and crystal 26. Mirrors 28, 29 and prism 31 function as an optical delay line. The 532-nm beam 21 is deflected off mirror 28 to pdsm 31 where it is internally reflected and follows a return path toward mirror 29 where it is reflected toward gating crystal 26. The imaging-bearing beam from sample 14 and the return reference beam from pdsm 31 are directed so as to overlap at crystal 26 and to be generally collinear passing through the crystal. A substantial collinear overlap of the interfering beams preserves the two-dimensional image data in the resulting time-gated beam. To minimize signal loss in the generally low-intensity image-bearing beam from the sample, mirror 29 may be formed by a dichroic mirror reflecting the second harmonic 532-nm reference beam, but not the infrared 1064-nm image-bearing beam. As illustrated in FIG. 1 mirror 28 is positioned between lens 24 and crystal 26. Mirror 28 may alternatively be positioned between sample 14 and lens 24. In this latter position the beam intensity is generally lower and thus there is less likelihood of burning the mirror; however, in this position a larger prism 31 or more complicated optical arrangement may be needed to control the spot size.

Prism 31 is mounted to be movable in the direction perpendicular to reference beam 21 indicated by arrow 32. Moving prism 31 adjusts the optical path length of the reference beam and varies the time at which the reference beam arrives at crystal 26. The upconverting crystal 26 generates an upconverted beam only when both the image-bearing probe beam and the reference beam are present together. Thus by varying the delay (i.e., optical path length) in the reference beam, the apparatus is able to selectively gate different portions of the transmitted image-bearing beam. Although the illustrated embodiment uses a movable pdsm arrangement to vary the optical path length, and hence delay, the skilled practitioner will recognize that suitable delays could be achieved by other arrangements and mechanisms. For example, multiple lasers could be used in place of the second harmonic generation, although multiple lasers may be more difficult to synchronize because of the short time scales involved. Moreover, the movable pdsm arrangement is advantageous because the two reflecting surfaces are angularly stable with respect to one another and this simplifies control over beam alignment as the delay is adjusted.

As already indicated, the upconversion is performed by crystal 26. The crystal receives the infrared probe beam and green reference beam and provides an upconverted image-bearing beam 33 of wavelength 355 nm. The crystal is driven at the fundamental (infrared) frequency and at the reference beam's second harmonic frequency. When driven sufficiently hard, the crystal may be caused to radiate at the sum (and difference) frequencies. Although the illustrated embodiment uses the sum- and difference-frequency generation as the upconversion process, the skilled practitioner will recognize that a number of other nonlinear processes may also be used to achieve upconversion.

For nonlinear optical processes that generate new optical waves such as sum- and difference-frequency generation, phase matching is essential to good conversion efficiency. Because of dispersion in the medium used for the nonlinear process (i.e., differences in the index of refraction which effect the velocities of the wave propagation at the different frequencies), the input and output waves generally do not propagate at the same velocity. Because the output wave has a specific phase relationship with respect to the input waves, the velocity difference leads to a dephasing between the output waves generated at different points in the medium. This leads to destructive interference, which limits the conversion efficiency. One method to compensate for the different phase velocities is to propagate the input and output waves at different angles such that the phase velocities are the same in a given direction. This approach does not work for two-dimensional imaging because the spatial information is blurred in one direction due to the angle between the input and output waves. The phase matching can be done collinearly, for example by using birefringence in a crystal to compensate for the dispersion. In this case there is no loss of spatial information, and two-dimensional imaging is possible.

With the collinear phase matching process in a crystal, other nonlinear processes in the crystal can also be used to produce a time gate. One could use difference-frequency conversion to produce an image at a lower frequency (downconversion). Although the advantage of upconversion is not gained in this case, the separation of the time-gated image radiation from the probe and pump radiation is aided because the image is at a different wavelength, and spectral filtering processes can be used. Spectral filtering can provide good discrimination against scattered background light. This approach may find application, for example, for imaging through thin samples. The collinear time-gate could also be used to produce an image at a new polarization (as could occur through difference-frequency mixing with an infrared probe beam and a 523 nm pump beam producing an infrared image beam with a polarization orthogonal to the probe beam). Crystal 26 would have to be placed between crossed polarizers to gain sufficient discrimination against the probe light if the probe and image beams were differentiated by polarization alone and not by frequency.

Detector 18 was provided by an image-intensified charge-coupled device (ccd) camera sensitive at the 0.355 nm wavelength. A lens 34 positioned after crystal 26 focuses the upconverted image-bearing beam 33 onto camera 18. A wavelength-selective mirror 36 and filter 37 are inserted after lens 34 to separate the 0.355 nm upconverted beam from the 1064 nm and 532 nm reference and probe beams.

Other types of detectors may also be employed. Typically the detector will be less than 100 percent efficient. For example, the quantum efficiency (the percentage of photons which will be detected) is less than 100 percent for silicon detectors or image intensifiers. In addition, any filters used to discriminate against background light will typically introduce loss for the beam to be detected. To obtain maximum detection of the image, it is beneficial to provide amplification of the image prior to detection. This can be done together with upconversion by using difference-frequency mixing (also called optical parametric amplification in this context). Those skilled in the art will see that amplification may also be provided by other means, such as an optical amplifier. In the case of the difference-frequency mixing, amplification may be performed without performing time gating by using a pump beam that has a long duration relative to the time over which scattered light exits from the sample.

In the illustrated arrangement the Fourier transform of the infrared signal after it passes through the sample is effectively being mixed with a plane wave at the second harmonic. This effectively shifts the image-bearing Fourier transform to the third harmonic frequency. In some configurations of the apparatus it may be desirable to focus the second-harmonic reference beam to obtain greater intensity and thereby drive the crystal harder for greater third-harmonic signal generation. For accurate image upconversion with no significant loss or distortion of image data in these configurations the second harmonic beam should be large enough that the probe beam Fourier components bearing the image data do not extend outside the reference beam.

The upconversion subsystem serves two important functions in the described system. First it enables usable detection of low-intensity image-bearing beams formed of unscattered or little-scattered photons at infrared or near-infrared frequencies by upconverting the image-bearing beams to a frequency at which efficient, sensitive detectors operate. Second, it achieves this function without destroying the essentially two-dimensional image information carried in the upconverted beam. Those skilled in the art given the benefit of the present disclosure will appreciate that other upconversion techniques familiar from other contexts can be adapted to achieve one or both of these functions.

The possibility of transillumination imaging in the infrared range roughly from 1000 to 2000 nm, and in particular direct two-dimensional transillumination imaging in this range, without the use of time-resolving techniques has not generally been appreciated in the past. For imaging with the longer infrared wavelengths, however, the apparatus of FIG. 1 may advantageously be used without the time-gating. This is particularly the case for transillumination imaging in the body where one tends to find less scatter and increased absorption for longer infrared wavelengths. This improves the spatial resolution because on the average the scattered photons traverse a longer distance within the sample so that they are more likely to be absorbed before exiting the sample. Thus, in this wavelength range useful images may already be obtained by upconverting the image-bearing beam to the range of visible light where efficient detectors are available without the necessity of time-gating.

The imaging capability of the above apparatus has been demonstrated with a sample consisting of a resolution test target 38 (shown in phantom in FIG. 1) behind which is placed a fat emulsion 39 to simulate scattering through tissue. The sample in this example is used to demonstrate the approach described here. In general, the specimen to be imaged need not be separate from the scattering medium, but may include the scattering medium. Resolution test target 38 (a portion of which is shown in FIG. 2) consists of a mask of opaque material in which is formed a pattern of linear horizontal and vertical openings 40 and 41 of known spacings. Test target 38 allows one to determine the spatial resolution possible for a given quantity of scatterer. The fat emulsion sample 39 was a commercial intravenous fat emulsion preparation available under the trademark Liposyn® II from Abbott Laboratories and consisting of a fat emulsion with approximately 400-nm fat particles. A mixture produced by diluting 20 percent Liposyn® II in water was placed in a cuvette behind the resolution test target.

FIG. 3 shows an image of the test target of FIG. 2 taken through the Liposyn® II mixture with the cw mode-locked laser. The image illustrated in FIG. 3 (and in FIGS. 4A, 4B, 4C and 5 below) is a display of the image data recorded by ccd camera 18. The image of FIG. 3 was obtained with a 4-centimeter (cm) thickness of 0.6 percent Liposyn® II in water prepared by diluting the 20% Liposyn® II. About 4 Watts (W) of the 1064-nm probe beam was incident on the sample, and about 1 W of the 532-nm reference beam was used for the upconversion. The image was integrated over a time of 1000 seconds. For this test run the uniformity of the laser illumination was not optimized, and this leads to the noticeably mottled appearance of the image. The resolution bars in FIG. 3 are spaced with 1.26 and 1.41 pairs per millimeter, corresponding to a resolution of about 0.4 millimeters (mm).

The attenuation coefficient for this Liposyn® II mixture was determined at the 1064 nm wavelength by directing the probe beam through a portion of the 0.6-percent Liposyn® II mixture placed in a 1-mm-wide cuvette. The unscattered 1064-nm light was detected at about 50 cm from the cuvette. From this measurement it may be determined that the photon transport mean free path in this Liposyn® II mixture is 2 mm. Thus the image in FIG. 3 corresponds to a total of 20 photon transport mean free paths through the sample. This is a factor of 2 below that previously believed to be required for transillumination breast imaging.

The measurements performed with the cw mode-locked laser are limited by the dark current noise of the intensified camera and by the relatively low conversion efficiency of the nonlinear KDP crystal at the relatively low peak intensities of the cw laser. The conversion efficiency was greatly increased using the Q-switched mode-locked laser. In addition, because the Q-switched laser produces intense pulses during a fraction of a nanosecond with 0.1 second between pulses, the dark noise of the camera can be greatly reduced by electronically gating the camera for a brief period coinciding with the laser pulse. This electronic gating of the camera is performed on the nanosecond scale, while the optical time-gating discussed above to achieve good spatial resolution is performed on the order of tens of picoseconds so that the camera gating is long compared with the optical time-gating.

The results of test runs with the Q-switched laser are shown in FIGS. 4A, 4B and 4C. These images show the same portion of the resolution test target as used for FIG. 3. FIG. 4A shows the image of the test target taken without the intervening Liposyn® II scatterer. FIG. 4B shows an image taken through the 0.6 percent Liposyn® II mixture with an optimal gate position. The spatial resolution is not discernably degraded from FIG. 4A although the signal-to-noise ratio is reduced because there are fewer detected photons. FIG. 4C shows an image taken 66 ps after the optimal gate position allowing significant scattered photons through the time gate. There is no readily distinguishable image in FIG. 4C. Comparison of FIGS. 4B and 4C gives a graphic demonstration of the system's ability to enhance spatial resolution.

The images in FIGS. 4B and 4C were taken with an integration time of 100 seconds and with 5 milliJoules (mJ) of energy per pulse of infrared light incident on the target. This corresponds to a reduction by a factor of 8000 in the total number of photons required for FIG. 4B over that used for FIG. 3. This demonstrates the large improvement in detection efficiency provided by the Q-switched mode-locked laser over the cw mode-locked laser.

The test results described herein are offered merely to demonstrate the feasibility of the method, and it is emphasized that the parameters used in the illustrated tests have not been optimized for maximum performance. For example, the upconversion efficiency with the described time gate is about 7 percent, and there is a loss by a factor of 30 through the filters used to eliminate the 532 nm light. Further improvement may be made by using a difference-frequency upconversion time gate, which can achieve gain in the time-gate process, overcome losses in both the time gate and filters, and realize an improvement by a factor of 500 in detection efficiency. FIG. 5 shows an image taken through the same Liposyn® II mixture described above with a difference-frequency time gate using the Q-switched mode-locked laser. The 1064-nm infrared probe beam was used for imaging. After passing through the scattering medium, the infrared beam was mixed with 355-nm (third harmonic) ultraviolet radiation in the KDP crystal. The difference-frequency mixing process generated an image at 532 nm, which was detected by the intensified ccd camera and is shown in FIG. 5. The image of FIG. 5 was taken with a single pulse from the Q-switched laser. This amounts to a factor of 200 less energy than was used for the image of FIG. 4B.

The above descriptions and drawings disclose illustrative embodiments of the invention. Given the benefit of this disclosure, those skilled in the art will appreciate that various modifications, alternate constructions, and equivalents may also be employed to achieve the advantages of the invention. For example, apparatus may be configured with other forms of time-gating such as by means of Kerr cells or other time-correlation methods; other upconversion crystal materials are known that may be used instead of the KDP crystal or other upconversion techniques may be adapted to the present use; and other optical arrangements may be employed for focusing and filtering the various beams. Although the invention is illustrated here by reference to medical imaging, those skilled in the art will appreciate that the methods and apparatus discussed here may be adapted to imaging applications other than medical-for example, imaging through sea water, fog, or even air pollution haze, clouds, or smoke. Therefore, the invention is not to be limited to the above description and illustrations, but is defined by the appended claims.

What is claimed is:

1. Transillumination imaging apparatus for obtaining a two-dimensional image of a sample through a scattering medium, comprising:

a probe radiation source for applying a probe beam of radiation to the sample, said probe beam having a frequency in the infrared to near-infrared range;

optical means for spreading said probe beam to cover an area of said sample extending in two dimension, wherein said probe beam is representative of a two-dimensional image of said area after interaction with said sample;

time-gate means for selecting a temporal portion of said probe beam in a narrow time window representative of early arriving photons transmitted through said scattering medium and providing a time-gated beam representative of a two-dimensional image of said sample area;

wherein said time-gate means comprises:

a reference radiation source providing a reference beam of radiation at a reference frequency directed along an optical path that avoids said sample and said scattering medium, said reference frequency being higher than said infrared to near-infrared range; and coupling means for collinearly mixing said reference beam and said probe beam after interaction with said sample to provide said time-gated beam;

means for adjusting the length of said reference beam optical path so as to adjust the length of the narrow time window of the selected temporal portion of said probe beam;

upconversion means for shifting said time-gated beam to an upcoversion frequency higher than said probe beam frequency without destroying said two-dimensional image; and a detector operative at said upconversion frequency for detecting said upconverted time-gated beam representative of said two-dimensional image at said upconversion frequency.

2. The apparatus of claim 1, further comprising a crystal receiving said reference beam and said probe beam after interaction with said sample, said crystal interacting nonlinearly with said reference and probe beams to provide said upconverted time-gated beam.

3. The apparatus of claim 2 wherein said probe radiation source and said reference radiation source are provided by a single laser.

4. The apparatus of claim 3 wherein said laser comprises a Q-switched mode-locked laser.

5. The apparatus of claim 3 wherein said means for adjusting the length of said reference beam optical path comprises a prism mounted for movement in a linear direction and disposed in said optical path such that said optical path enters and exits said prism parallel to said linear direction, whereby said path length may be adjusted by moving said prism in said linear direction.

* * * * *